United States Patent [19]
Aspnes

[11] 3,985,447
[45] Oct. 12, 1976

[54] MEASUREMENT OF THIN FILMS BY POLARIZED LIGHT

[75] Inventor: David Erik Aspnes, Berkeley Heights, N.J.

[73] Assignee: Bell Telephone Laboratories, Incorporated, Murray Hill, N.J.

[22] Filed: Aug. 29, 1975

[21] Appl. No.: 609,037

[52] U.S. Cl. .............................. 356/118; 356/119
[51] Int. Cl.² ..................................... G01N 21/40
[58] Field of Search ........................ 356/114–118, 356/30–31, 33–35; 250/225

[56] References Cited
OTHER PUBLICATIONS

Ord et al. "A Computer–Operated Following Ellipsometer" Applied Optics, 10–67, pp. 1673–1677.
Richartz; M. "Mesmethoden des MacCullaghschen Kompensators" Zeitschrift fur Instrumentenkunde vol. 74, 4–66, pp. 120–125.
Aspnes et al. "High Precision Scanning Ellipsometer" Applied Optics, vol. 14, 1–75, pp. 220–228.
Kent et al. "A Photoelectric Method for the Determination of the Parameters of Elliptically Polarized Light," Jr. Optical Soc. of America vol. 27, 3-1937 pp. 117–119.
Reinberg, A. R. "Ellipsometer Data Analysis with a Small Programmable Desk Calculator", Applied Optics vol. 11, 5–72, pp. 1273–1274.
Born et al. "Principles of Optics," MacMillan Co. 1964 pp. 554–555.

*Primary Examiner*—John K. Corbin
*Assistant Examiner*—Wm. H. Punter
*Attorney, Agent, or Firm*—D. I. Caplan

[57] ABSTRACT

In order to measure the thickness and refractive index of a thin film on a substrate, such as a film of silicon dioxide on a substrate of silicon, a beam of substantially monochromatic polarized light is directed on the film. The reflected light is transmitted through an optical compensator and an optical analyzer both of which are rotating at different angular speeds, $\omega_A$ and $\omega_C$, respectively; and the transmitted optical intensity is measured as a function of time. A Fourier analysis, for example, of the profile of this optical intensity vs. time can then be used for determining the Stokes parameters of the light reflected by the thin film and thereby also the thickness and refractive index of the film.

13 Claims, 2 Drawing Figures

MEASUREMENT OF THIN FILMS BY POLARIZED LIGHT

BACKGROUND OF THE INVENTION

1. Field of the Invention

This invention relates to the field of the measurement of the characteristics of thin films and, more particularly, to the measurement of the thickness and refractive index of thin films by means of optical techniques.

2. Description of the Prior Art

In order to measure the thickness and refractive index of a thin film on a substrate, various optical techniques have been employed in the prior art. Ordinarily these techniques involve measurements of the intensity and polarization of the transmitted or reflected light from the thin film, as a function of angular orientation ("ellipsometry"). However, the use of these techniques generally tends to be unduly time-consuming. While the more rapid techniques using rotating analyzer ellipsometry have been used in the prior art, such techniques suffer from ambiguities and do not yield correct results in the presence of diffuse reflectance.

In U.S. Pat. No. 3,873,209 issued to Schinke et al. on Mar. 25, 1975, an optical thin film waveguide technique was described for measuring the thickness and refractive index of a thin film. In that technique, an evanescent optical wave is coupled into the film; and the resulting optical intensity minima, characterizing the light which is coupled out of the film as a function of angle, yield data from which the desired thin film thickness and refractive index can be determined. It would be desirable, however, to have a relatively fast thickness measurement technique which does not require the operator to locate such minima.

SUMMARY OF THE INVENTION

In order to measure the thickness and refractive index of a thin film on a substrate, a substantially monochromatic beam of linearly polarized light is incident on the film. The beam undergoes multiple reflections both at the interface of the film with the ambient atmosphere and at the interface of the film with the substrate. The invention is applicable to the cases where either, both, or none of these reflections has a diffuse (nonspecular) component. The resulting reflected beam from the thin film-substrate system is then allowed to pass through a rotating optical compensator and an advantageously faster rotating optical analyzer. The optical beam intensity transmitted by the rotating analyzer is measured by an optical detector as a function of time. An analysis of this function of time yields the Stokes parameters of the light reflected by the thin film-substrate system, from which both the thickness and refractive index of the thin film can be determined.

In a specific embodiment of the invention, a beam of substantially linearly polarized monochromatic light is directed onto the surface of a thin film on a substrate. The film need not be completely transparent and there may be multiple diffuse reflections occurring in the film. The reflected optical beam from the thin film-substrate system is passed through, in spatial sequence, a rotating optical compensator and a rotating optical analyzer, the analyzer rotating at substantially three times the angular speed of the compensator. The optical beam intensity transmitted by the rotating analyzer is measured as a function of time. This function is then Fourier analyzed, and the Fourier coefficients are then used to calculate the desired refractive index and thickness of the thin film.

BRIEF DESCRIPTION OF THE DRAWING

This invention together with its features, objects, and advantages may be better understood from the following detailed description when read in conjunction with the drawing in which.

DETAILED DESCRIPTION

Figure 1:
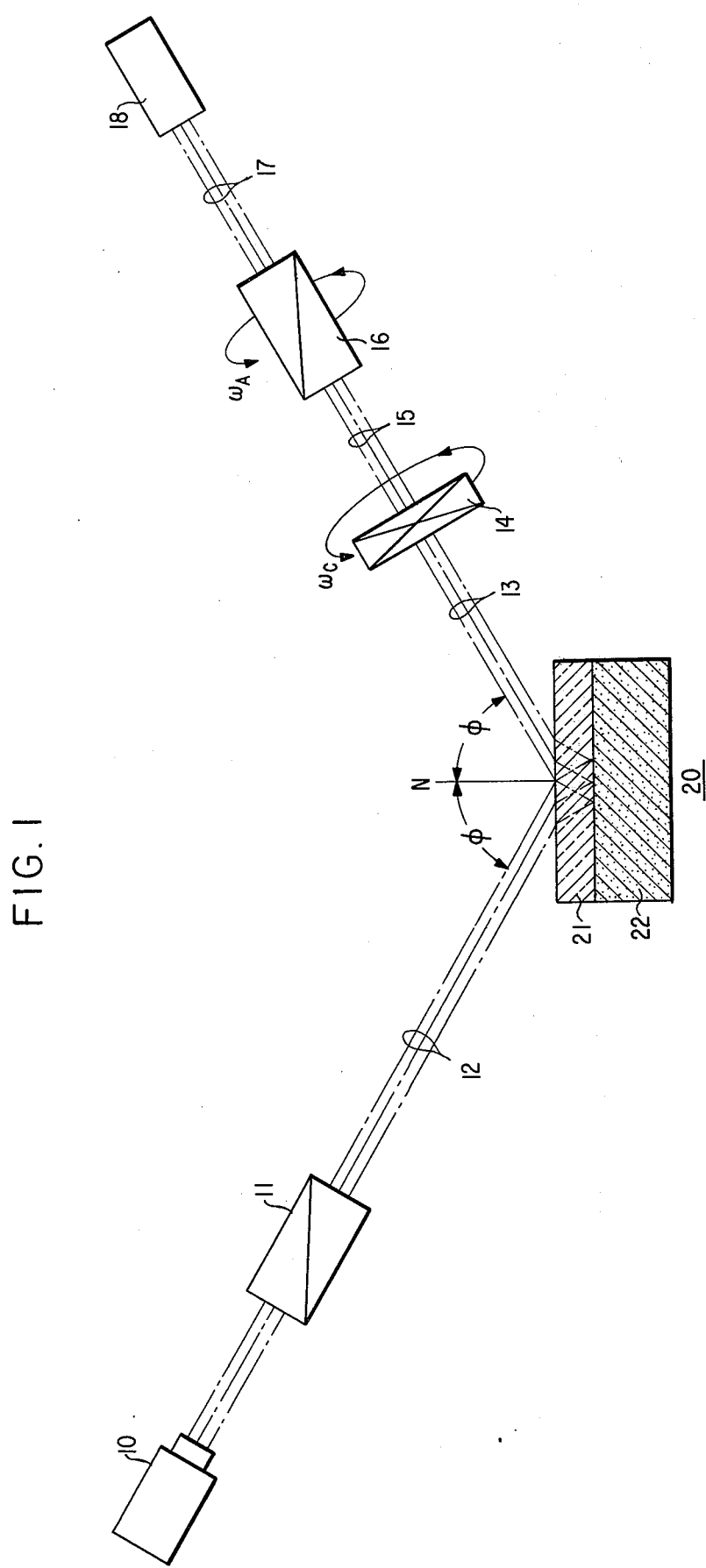
FIG. 1 illustrates a thin film being tested in accordance with a specific embodiment of the invention.

As shown in FIG. 1, a source 10 of substantially monochromatic optical radiation directs its output radiation through an optical (nonrotating) polarizer 11, to produce a linearly polarized monochromatic optical beam 12. This beam 12 is incident at an angle $\phi$ to the normal of an exposed major surface of a thin film-substrate system 20 comprising a thin film 21 on a substrate 22. For example, the thin film is essentially silicon dioxide and the substrate is essentially monocrystalline semiconductive silicon. Upon multiple internal reflections in the film 21, a reflected beam 13 emerges and passes through an optical phase compensator 14. This compensator is designed so as to introduce a relative phase delay $\delta$, typically of about $\pi/2$ radians, between a pair of mutually perpendicularly polarized optical beam components. While the beam 13 passes through, the compensator 14 is rotated at an angular velocity $\omega_C$ about an axis substantially parallel to the direction of propagation of the beam. A beam 15 is thus transmitted by, and emerges from, the compensator 14 and is then incident on an optical analyzer (polarizer) 16 rotating at an angular velocity $\omega_A$ about the same axis as that of $\omega_C$. A beam 17 is thus transmitted by the rotating analyzer 16 and is incident upon utilization means 18 for detecting the optical intensity substantially continuously as a function of time. The utilization means thereupon also performs a Fourier analysis of this optical intensity vs. time, and processes the analysis to yield the refractive index and thickness of the thin film 21 as discussed below in greater detail.

As an example, for the purpose of illustration only, the optical source 10 produces substantially monochromatic visible light, for example, a filtered xenon arc yielding typically a 6000 Angstrom beam with a wavelength spread of advantageously less than 10 Angstroms, perferably less than 5 Angstroms. The azimuth angle P of polarizer 11 is oriented so that the plane of the electric vector associated with the linearly polarized beam 12 is at an angle of about 30° with respect to the plane of incidence determined by the propagation direction of the beam 12 and the normal N to the exposed surface of the thin film 21. This thin film is essentially silicon dioxide which has been grown on a silicon substrate so that the beam undergoes multiple reflections at the ambient-oxide interface and at the substrate-oxide interface and emerges as the reflected beam 13. The compensator 14 is a standard quarter-wave plate rotating at angular speed $\omega_C$ which is one-third the angular speed $\omega_A$ of the analyzer 16. The analyzer 16 and the compensator are advantageously rotated around a common axis by a pair of drive chains driven by a single motor, the drive chains having relative tooth or gear ratios of 3:1 for this purpose of obtaining $\omega_A = 3\omega_C$. Typically, $\omega_C$ itself is about 150 radians per second, but other speeds are obviously useful in this invention.

In order to understand in general the selection of optimum parameters, or approximations thereto, which are useful in the practice of the invention, the subscript $\sigma$ will be used to describe those parameters which are associated with the component of the various optical beams which has its electric vector perpendicular (German "senkrecht") to the plane of incidence, whereas the subscript $\pi$ will be used for those parameters associated with electric vector parallel to the plane of incidence. The optical amplitude reflectances (which may be complex) for the $\sigma$ and $\pi$ components of the beam 12 are denoted by $r_\sigma$ and $r_\pi$, respectively, with respect to the three-phase system of ambient-thin film-substrate. It is convenient to define a polarization reflectance ratio $\rho$ as the ratio of $r_\pi$ to $r_\sigma$, which can be a complex number:

$$\rho = r_\pi / r_\sigma = \tan\psi e^{i\Delta} \quad (1)$$

This reflectance ratio $\rho$ is of much importance in the determination of the refractive index and thickness of the thin film 21, as discussed below.

In the case of a simple two-phase system, with both phases characterized by real number scalar dielectric constants, then the reflectance ratio $\rho$ is a real number, so that the argument $\Delta$ of the exponential of $\rho$ (which should be conveniently limited to range 0 to $-\pi$) is either 0 or $-\pi$ radians, changing suddenly from 0 to $-\pi$ as a function of angle of incidence $\phi$ when $\phi$ goes through Brewster's angle. More generally (including cases for complex $\rho$), the principal angle of incidence $\phi_P$ is defined as that angle at which $\Delta = -\pi/2$ (or jumps suddenly from 0 to $-\pi$), and the pseudo-Brewster angle $\phi_B$ is defined as that angle of incidence at which $\tan \psi$ (the real part of $\rho$) is a minimum. The difference between $\phi_B$ and $\phi_P$ is ordinarily quite small, and these angles are of interest in this invention in that the principal angle $\phi_P$ corresponds to that value of the angle of incidence of the two-phase substrate-ambient system for which the optimum accuracy can be obtained in the measurement of the refractive index of the thin film 21 on the substrate 22 in the three-phase system of ambient-oxide-substrate. However, this accuracy is not very sensitive to the angle of incidence, $\phi$, so that useful results can be obtained even if $\phi$ deviates from the optimum value $\phi_P$ by as much as 10° or 20° or more.

While the invention can be practiced with a variety of relative values of angular speeds $\omega_A$ and $\omega_C$, it is convenient to use $\omega_A = 3\omega_C$, that is:

$$A = \omega_A t = 3\omega_C t \quad (2)$$

$$C = A/3 + C_0 \quad (3)$$

where $C$ is the azimuth angle of the major (fast polarization) axis of the compensator 14 relative to the plane of incidence, and $A$ is the instantaneous azimuth angle of the polarization component which is transmitted by the analyzer 16 relative to the plane of incidence. Thus, at $t=0$, the analyzer transmits the polarization component whose electric vector is in the plane of incidence (plane of the Figure itself); whereas the compensator at $t=0$ is oriented such that the fastest polarization of electric vector is at an angle of $C_0$ with respect to the plane of incidence. For ease of operation and calculation, it is convenient but not essential to set $C_0 = 0$ or at least not to exceed 30 degrees. With this setting of $C_0$, the intensity I (normalized to an arbitrary value $I_0$) of the transmitted beam 17 detected by means 18 will be a functon of time. It is this normalized intensity ($I/I_0$) which, as a function of time contains the desired information to be processed, by Fourier analysis as described below for example, for yielding the desired value of reflectance ratio $\rho$ and thence the refractive index and thickness of the thin film 21.

Theory

The instantaneous amplitude of the optical electric vector $E_t$ of the transmitted optical beam 17 is given by known principles:

$$\begin{aligned} E_t &= [E_\pi \cos C + E_\sigma \sin C]\cos(A-C) + e^{i\delta}[-E_\pi \sin C + E_\sigma \cos C]\sin(A-C) \\ &= E_\pi [\cos C \cos(A-C) - e^{i\delta} \sin C \sin(A-C)] \\ &+ E_\sigma [\sin C \cos(A-C) + e^{i\delta} \cos C \sin(A-C)] \end{aligned} \quad (4)$$

where $E_\pi$ and $E_\sigma$ are the instantaneous optical electric vectors respectively parallel to and perpendicular to the plane of incidence, and where $\delta$ is the known (measured) phase delay associated with the optical electric vector along the minor (slow) axis of the compensator 14 relative to the optical electric vector along the major (fast) axis of the compensator. The normalized intensity ($I/I_0$), which is equal to $2|E_t|^2/(|E_\pi|^2 + |E_\sigma|^2)$, is then given by:

$$\begin{aligned} (I/I_0) &= 1+(s_1/s_0)[\cos 2C \cos 2(A-C) - \cos\delta \sin 2C \sin 2(A-C)] \\ &+ (s_2/s_0)[\sin 2C \cos 2(A-C) + \cos\delta \cos 2C \sin 2(A-C)] \\ &- (s_3/s_0)[\sin\delta \sin 2(A-C)] \end{aligned} \quad (5)$$

where $s_0$, $s_1$, $s_2$ and $s_3$ are the so-called Stokes parameters, defined by:

$$s_0 = E_\pi {}^* E_\pi + E_\sigma {}^* E_\sigma \quad (6a)$$

$$s_1 = E_\pi {}^* E_\pi - E_\sigma {}^* E_\sigma \quad (6b)$$

$$s_2 = 2 Re\, E_\pi\, E_\sigma^* \quad (6c)$$

$$s_3 = -2 Im\, E_\pi\, E_\sigma^* \quad (6d)$$

Substituting in Equation (4) the expression for $C$ given by Equation (3), and defining a convenient quantity $\theta$ as:

$$\theta = 2A/3 = 2\omega_C t - C_0, \quad (7)$$

it is found from Equation (5) that:

$$\begin{aligned} I/I_0 &= 1+(s_1/s_0)[\cos^2(\delta/2)\cos 3\theta + \sin^2(\delta/2)\cos(\theta-4C_0)] \\ &+ (s_2/s_0)[\cos^2(\delta/2)\sin 3\theta - \sin^2(\delta/2)\sin(\theta-4C_0)] \\ &- (s_3/s_0)\sin\delta\sin(2\theta-2C_0). \end{aligned} \quad (8)$$

It is convenient to introduce Fourier coefficients $\alpha_1$, $\alpha_2$, $\alpha_3$, $\beta_1$, $\beta_2$, $\beta_3$, defined by:

$$\begin{aligned} I/I_0 &= 1+\alpha_1\cos\theta+\beta_1\sin\theta+\alpha_2\cos 2\theta+\beta_2\sin 2\theta \\ &+ \alpha_3\cos 3\theta+\beta_3\sin 3\theta. \end{aligned} \quad (9)$$

The values of all these Fourier coefficients can be measured by the utilization means 18, keeping in mind the definition of $\theta$ as a function of time given by equation (7). Comparing equations (8) and (9), it is found that the relative Stokes parameters are given by:

$$s_1/s_0 = \alpha_3[1+(\alpha_1^2+\beta_1^2)^{1/2}/(\alpha_3^2+\beta_3^2)^{1/2}] \quad (10a)$$

$$s_2/s_0 = \beta_3[1+(\alpha_1^2+\beta_1^2)^{1/2}/(\alpha_3^2+\beta_3^2)^{1/2}] \quad (10b)$$

$$s_3/s_0 = -(\alpha_2^2+\beta_2^2)^{1/2}/\sin\delta \; \text{sgn}(\beta_2) \quad (10c)$$

where only positive square roots (½ powers) are taken. Thus, the Fourier analysis of $I/I_0$ yields the values of the relative Stokes parameters. From these the desired value of reflectance ratio $\rho$ can be calculated from:

$$\rho = \frac{[(s_2/s_0)-i(s_3/s_0)]\tan P}{[(s_1/s_0)^2+(s_2/s_0)^2+(s_3/s_0)^2]^{1/2}-(s_1/s_0)} \quad (11)$$

where $P$ is the actual (measured) value of the azimuth angle of the polarized 11, and $i$ is the imaginary root. It should be noted at this point that the prior art ellipsometry techniques involving rotating only the analyzer assume that $(s_1/s_0)^2+(s_2/s_0)^2+(s_3/s_0)^2$ is equal to unity, which is not true in the presence of diffuse reflection. In addition, these prior art techniques determine only the magnitude of $s_3/s_0$ but not its algebraic sign ($s_0$ being always positive: Eq. (6a)), thereby producing the ambiguity of two possible values of the polarization reflectance ratio $\rho$ instead of solely the correct one. Thus, this invention yields unambiguously the single value of reflectance ratio $\rho$. From this value of $\rho$, the refractive index and thickness of the thin film 21 can be calculated, as set forth in a paper by A. R. Reinberg entitled "Ellipsometer Data Analysis with a Small Programmable Desk Calculator" in *Applied Optics*, Vol. 11, No. 5, pp. 1273–1274 (May 1972). Briefly, the calculation involves a method of successive approximation (Newton's method), starting with the known relationship of the reflectance ratio $\rho$ to the reflection parameters of the thin film-substrate system:

$$\rho = r_\pi/r_\sigma = \frac{Zr_{\pi,fs}+r_{\pi,af}}{1+Zr_{\pi,fs}r_{\pi,af}} \Big/ \frac{Zr_{\sigma,fs}+r_{\sigma,af}}{1+Zr_{\sigma,fs}r_{\sigma,af}} \quad (12)$$

where, for example, $r_{\pi,fs}$ is the reflection coefficient of the $\pi$ polarization of the two-phase film-substrate interface, the subscript pair $af$ refers to the two-phase ambient-film system, and where:

$$r_{\pi,fs} = \frac{\epsilon_s(\epsilon_f-\epsilon_a\sin^2\Phi)^{1/2}-\epsilon_f(\epsilon_s-\epsilon_a\sin^2\Phi)^{1/2}}{\epsilon_s(\epsilon_f-\epsilon_a\sin^2\Phi)^{1/2}+\epsilon_f(\epsilon_s-\epsilon_a\sin^2\Phi)^{1/2}} \quad (13)$$

$$r_{\sigma,fs} = \frac{(\epsilon_f-\epsilon_a\sin^2\Phi)^{1/2}-(\epsilon_s-\epsilon_a\sin^2\Phi)^{1/2}}{(\epsilon_f-\epsilon_a\sin^2\Phi)^{1/2}+(\epsilon_s-\epsilon_a\sin^2\Phi)^{1/2}} \quad (14)$$

$$r_{\pi,af} = \frac{\epsilon_f n_a\cos\Phi-\epsilon_a(\epsilon_f-\epsilon_a\sin^2\Phi)^{1/2}}{\epsilon_f n_a\cos\Phi+\epsilon_a(\epsilon_f-\epsilon_a\sin^2\Phi)^{1/2}} \quad (15)$$

$$r_{\sigma,af} = \frac{n_a\cos\Phi-(\epsilon_f-\epsilon_a\sin^2\Phi)^{1/2}}{n_a\cos\Phi+(\epsilon_f-\epsilon_a\sin^2\Phi)^{1/2}} \quad (16)$$

$$Z = \exp[4\pi i(\epsilon_f-\epsilon_a\sin^2\phi)^{1/2}d/\lambda] \quad (17)$$

where $n_a$ is the known refractive index of the ambient, $\phi$ is the actual angle of incidence, and where $\epsilon_f$ is the unknown thin film dielectric constant relative to vacuum, $d$ is the unknown thickness of the film, $\epsilon_s$ is the known substrate dielectric constant relative to vacuum, $\epsilon_a=n_a^2$ is the known ambient dielectric constant, and $\lambda$ is the known vacuum wavelength of the substantially monochromatic light. Accordingly, there are two ultimate unknowns, $\epsilon_f$ and $d$, and the intermediate unknown $Z$. From equation (17), however, it is seen that $Z$ must have an absolute magnitude of unity ($|Z|=1$) (so long as $\epsilon_f=n_f^2$ is greater than $\epsilon_a\sin^2\phi = n_a^2\sin^2\phi$, which will always be true for usual cases of interest involving a thin film whose refractive index is greater than that of the ambient). Moreover, putting into equation (12) the measured value of reflectance ratio $\rho$, and substituting into equation (12) the various expressions for the reflection coefficients of equations (13–16), then a quadratic equation in $Z$ results containing only $\epsilon_f$ as the only other unknown. In order to solve this equation, a first trial value of $\epsilon_f$ is assumed and a consequent first approximation to both $Z$ and $d|Z|/d\epsilon_f$ is calculated for this trial value of $\epsilon_f$, the first approximation to $Z$ being selected as the root of the quadratic equation in $Z$ which is closer to $|Z|=1$, and $d|Z|/d\epsilon_f$ being determined therefrom by known differential calculus methods. Then a second trial value of $\epsilon_f$ is adopted using the straight line slope approximation of $d|Z|/d\epsilon_f$ and the above first approximation of $Z$ (Newton's method) to try to make $|Z|=1$ with this second trial value. A third trial value of $\epsilon_f$ is then adopted if the magnitude of the second approximation of $Z$ (root closer to $|Z|=1$) on the second trial is not sufficiently close to unity within the desired accuracy, then using the second value of $\epsilon_f$ for the $d|Z|/d\epsilon_f$ straight line approximation. For each (complex) value of $Z$ thus found, using the corresponding trial value of $\epsilon_f$, then $d$ can be found from equation (17). When the trial values $\epsilon_f$ and the corresponding values of $d$ converge sufficiently to a limit, in accordance with desired accuracy, then the process of successive approximation is terminated, and the last trial value of $\epsilon_f = n_f^2$ provides the desired refractive index, $n_f$, of the thin film, whereas the value of $d$ corresponding to this last trial value of $\epsilon_f$ is the desired thickness of the thin film.

While the invention has been described in detail in terms of a specific embodiment, various modifications can be made without departing from its scope. The substrate can be any material which reflects light from the source beam 12, whether the reflection is specular, diffuse, polarizing, or depolarizing, such as glass, metal, plastics or liquids. The thin film can be any material which forms a transparent or semitransparent layer on the substrte. Determination of the thickness and dielectric constant of films which are not transparent is also possible but requires the use of measurements, at more than a single wavelength or angle of incidence. The invention is not restricted to angular speeds $\omega_A$ and $\omega_C$ with $\omega_A/\omega_C=3$, but other relative speeds can be used such as $\omega_A/\omega_C=4, 5, 6, \ldots$, or $7/2, 9/2, 11/2, \ldots$, or other rational number; but it should be noted that certain ratios or $\omega_A/\omega_C$, such as $\omega_A/\omega_C = 2$, should be avoided, in order to reduce undesired ambiguities.

Figure 2:
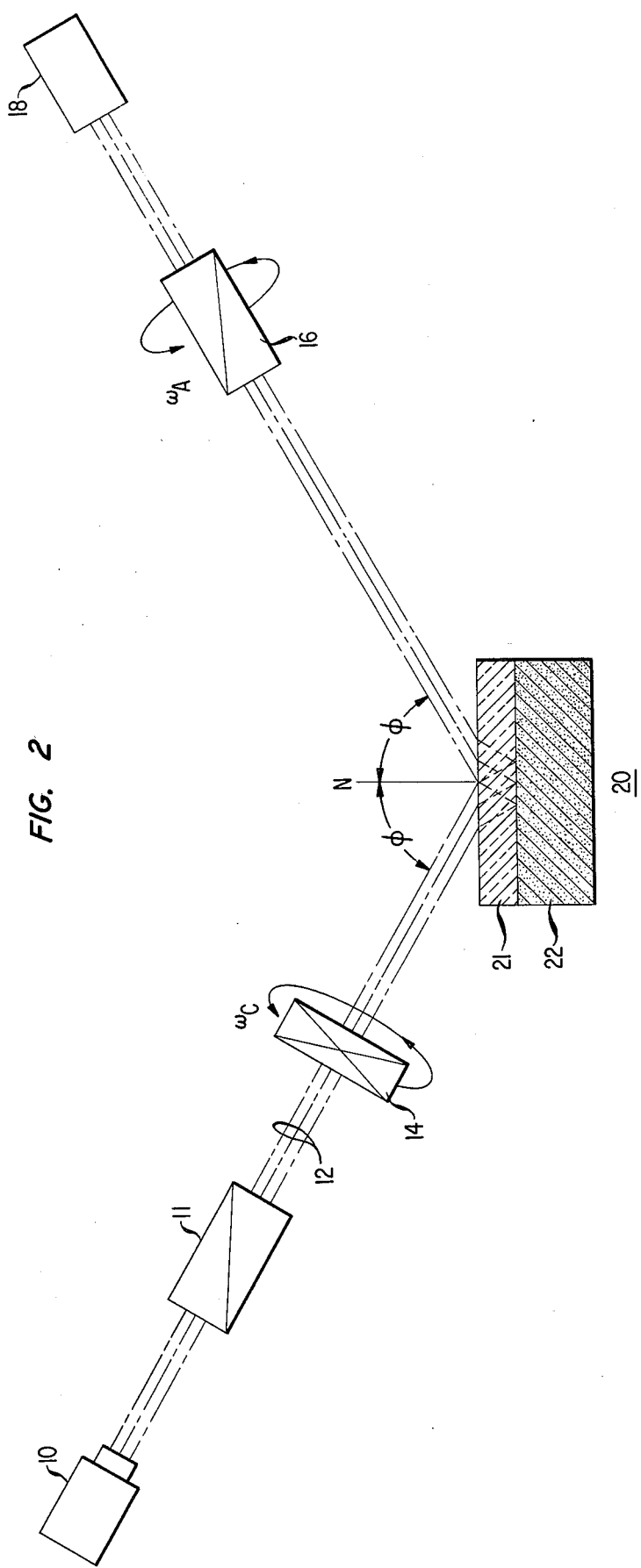
FIG. 2 illustrates a thin film being tested in accordance with another specific embodiment of the invention.

In the case where there is no diffuse reflectance, the compensator can be placed before (instead of after) the reflection, along the propagation direction, in the practice of the invention (as indicated in FIG. 2). Moreover, instead of linear polarization, the polarizer 11 can produce other known types of polarization, such as circular or elliptical.

It should be understood that there is a single remaining ambiguity in the calculation of the thickness $d$ from $Z$ in equation (17) due to the periodicity of the imaginary exponential, thereby yielding a spectrum of discrete possible values of $d$. Such an ambiguity can be removed, for example, by using a second different wavelength and obtaining a second discrete spectrum of values of $d$ and selecting the value of $d$ common to the two spectra.

What is claimed is:

1. A method of testing a thin film-substrate system which comprises the steps of
   a. directing an incident beam of substantially monochromatic polarized optical radiation onto an exposed surface of the thin film, and
   b. detecting the resulting reflected beam of radiation reflected from the surface and transmitted through a rotating optical compensator and a rotating optical analyzer, the compensator and analyzer rotating about an axis along the propagation direction of the reflected beam at different first and second different angular speeds, respectively.

2. The method of claim 1 in which the step of detecting includes measuring the intensity of resulting beam as a function of time and in which the incident beam is substantially linearly polarized.

3. The method of claim 2 in which the reflected beam passes through the rotating compensator prior to passing through the rotating analyzer.

4. The method of claim 3 wherein said compensator is rotating at a lower angular speed than that of the analyzer.

5. The method of claim 4 in which the compensator is rotating at substantially one-third the angular speed of the analyzer.

6. A method of testing a body including a thin film which comprises the steps of
   a. directing a substantially linearly polarized monochromatic beam of optical radiation onto an exposed surface of the thin film whereby a reflected beam is produced by reflection at said surface;
   b. rotating an optical compensator in the path of the reflected beam at a predetermined first angular speed about an axis parallel to the propagation direction of the reflected beam, while said reflected beam traverses through said compensator;
   c. rotating an optical analyzer in the path of the beam coming from the rotating compensator at a predetermined second angular speed different from the first angular speed about the said axis; and
   d. detecting the intensity of the beam transmitted by the rotating analyzer as a function of time.

7. The method of claim 6 in which said detecting is performed over a time interval including at least one complete rotation of the compensator.

8. The method of claim 6 in which the angular speed of rotating the analyzer is greater than that of the compensator.

9. The method of claim 8 in which the angular speed of rotating the analyzer is substantially three times that of the compensator.

10. A method of testing a thin film on a substrate body which comprises the steps of:
    a. directing a beam of polarized substantially monochromatic optical radiation through a rotating optical compensator onto a surface of the thin film; and
    b. detecting the optical radiation reflected by the body after the reflected radiation passes through an optical analyzer rotating at an angular speed which is substantially different from the angular speed of the rotating compensator.

11. The method of claim 10 in which the reflected radiation is detected substantially continuously for a period of at least a full rotation of the analyzer.

12. The method of claim 11 in which the beam incident on the rotating compensator is substantially linearly polarized.

13. The method of claim 12 in which the analyzer is rotating at substantially three times the angular speed of the compensator.

* * * * *